United States Patent [19]

Rosenberg

[11] Patent Number: 4,610,248
[45] Date of Patent: Sep. 9, 1986

[54] SURGICAL FINGER ASSEMBLY

[75] Inventor: Norman Rosenberg, East Brunswick, N.J.

[73] Assignee: University of Medicine and Dentistry of New Jersey, Newark, N.J.

[21] Appl. No.: 651,791

[22] Filed: Sep. 18, 1984

[51] Int. Cl.$^4$ ............................................. A61B 17/12
[52] U.S. Cl. ...................................................... 128/325
[58] Field of Search ............... 128/325, 326, 327, 346, 128/686, 112; 604/1

[56]   References Cited

U.S. PATENT DOCUMENTS

| | | | |
|---|---|---|---|
| 3,052,236 | 9/1962 | Schrieber | 128/118 |
| 3,411,505 | 11/1968 | Nobis | 128/325 |
| 3,490,448 | 1/1970 | Grubb | 128/325 |
| 4,120,320 | 10/1978 | Ziegler | 128/325 |

FOREIGN PATENT DOCUMENTS 782804  11/1980  U.S.S.R. ............... 128/325

OTHER PUBLICATIONS

*The Lancet,* vol. II, No. XXV, Dec. 17, 1955, "Prevention of Bleeding During Vein-Stripping", Foote, R. Rowden, Freedman, Marcus.

*Primary Examiner*—Robert P. Swiatek
*Assistant Examiner*—Cary E. Stone
*Attorney, Agent, or Firm*—David A. Jackson

[57]   ABSTRACT

A surgical finger assembly for control of bleeding of a lacerated blood vessel comprises a finger tip member prepared from pliant material and having a first pliant major surface dimensioned to conform to substantially the entire lacerated area of said blood vessel in a continuous compressive manner and a second opposite major surface; and an elongated handle defining at one end thereof a support section for attachment to the finger tip member at the second major surface, and the remainder of the handle defining a handle section for manipulating the said surgical finger assembly.

5 Claims, 7 Drawing Figures

SURGICAL FINGER ASSEMBLY

FIELD OF INVENTION

This invention relates to a surgical finger assembly for the control of bleeding from a blood vessel in the depths of a surgical or trauma wound.

BACKGROUND OF THE INVENTION

It is a usual procedure for a surgeon to employ one or more of his fingers to temporarily stop the bleeding in the depths of a wound from a laceration in an artery or vein. This procedure gives the surgeon time to remove any accumulation of blood from the wound area by the use of appropriate vacuum devices. Upon such removal of blood which usually obstructs the surgeon's view of the wound area, he is able to identify the character of the wound, and by partial and/or intermittent release of finger pressure from the wound, the bleeding may be attended to by hemostatic suturing or clamping. The shortcomings of this procedure include: the surgeon's fingers are part of a relatively bulky hand that must enter the wound cavity to a point where it obscures the surgeon's visibility; and the configuration of the surgeon's finger may not be appropriate because of the length and/or shape of the wound.

The present invention provides a novel surgical finger assembly that is especially adapted for controlling the bleeding from a blood vessel in the depths of a surgical or trauma induced wound, without requiring the entry of a surgeons hand into the wound cavity. Further, the surgical finger assembly of the instant invention may be selected from a plurality of different sized and configured surgical finger assemblies, thus permitting the surgeon to select the configuration of such an assembly most appropriate to a particular wound configuration to be attended to.

OBJECTS OF THE INVENTION

An object of the invention is to provide a nqvel surgical finger assembly for the control of bleeding from a blood vessel in the depths of a surgical or trauma induced wound.

Another object of the invention is to provide a novel finger assembly including a pliant finger tip member having a geometrical configuration that is particularly suited, in accordance with a surgeon's diagnosis of the character of a wound and the remedial procedures required, to control the bleeding from a wound of a particular configuration, and to assist in the hemostatic suturing or clamping of such wound.

SUMMARY OF THE INVENTION

These and other objects of the present invention are achieved by a novel surgical finger assembly comprised of a finger tip member comprised of a pliant material and an elongated handle having one end portion thereof attached to a top surface of the finger tip member. The finger tip member may be fixedly attached to the elongated handle or removably attached to such handle as a disposable unit. The elongated handle is of such a length, angulation and thickness that it is suitable to extend the finger tip member into the depths of a wound for applying in a compressive manner, a pliant exterior surface of the finger tip member against substantially the total area of the wound for controlling the blood flow therefrom. Additionally, the geometrical configuration of the pliant finger tip member is by appropriate selection from a plurality of such pliant finger tip members of different sizes and configurations, particularly suited to be utilized in controlling the bleeding from a wound of a particular configuration.

BRIEF DESCRIPTION OF THE DRAWINGS

A better understanding of the present invention as well as other objects and advantages thereof will become apparent upon consideration of the detailed disclosure thereof, especially when taken with the accompanying drawings, wherein.

DETAILED DESCRIPTION OF THE DRAWINGS

Figure 1:
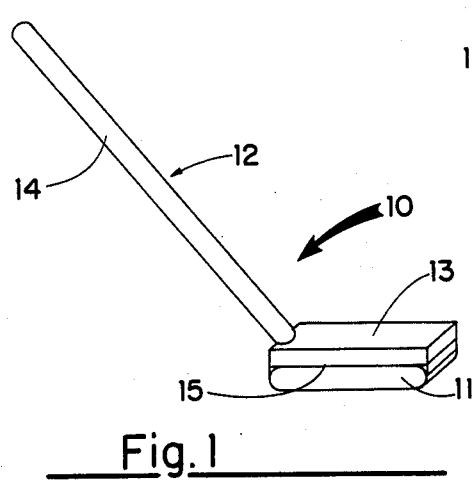
FIG. 1 is an elevational view of a surgical finger assembly of the present invention.

Referring now to the drawings, there is illustrated in FIG. 1 a surgical finger assembly of the present invention, generally indicated as 10, comprised of a finger tip member 11 of pliant material and an elongated handle 12. The elongated handle 12 includes a support section 13 at one end thereof and an elongated handle section 14 extending to the other end thereof. The support section 13 is fixedly attached to a major surface 15 of the finger tip member 11 by means of an adhesive. (Alternately, the support section 13 may be removably attached to the major surface 15 of the finger tip member 11 by means of bands, clips, or snap-lock devices, to provide a surgical finger assembly wherein the pliant finger tip member is a replaceable, disposable unit.)

The finger tip member 11 may be comprised, for example, of a solid but flexible rubber or plastic material; or of a fluid or gel-filled nonporous container formed of a silicone membrane, rubber or plastic material. The geometric configuration of the pliant finger tip member 11, more particularly its length, width and thickness, are selected to assure that the contact area between the finger tip member 11 and a lacerated area of a blood vessel to be surgically attended to will adequately cover the wound in a continuous compressive manner, thus controlling the bleeding eminating therefrom.

The elongated handle 12 may, for example, be comprised of a rigid or semiflexible metal or plastic material, which is of sufficient length for introducing the pliant finger tip member 11 into the depths of a surgical or trauma induced wound, so as to engage, in a compressive manner, a lacerated area of a blood vessel. A minimum thickness of the elongated handle 12 is desirable to assure that the surgical finger assembly 10 takes up very little space when it is introduced into the depths of such wound, thus assuring the surgeon maximum visibility into the wound. The elongated handle 12 of the embodiment of the instant invention illustrated in FIG. 1, is of a unitary structure with the support section 13 and the elongated handle section 14 forming an obtuse angle with respect to each other. An alternative to such unitary structure within the contemplation of the instant invention is an elongated handle 12 comprising a support section 13 that is removably attached to the elongated handle section 14, thus rendering disposable and replaceable the end of the surgical finger assembly 10 that includes the pliant finger tip member 11. As will be apparent to those skilled in the art, the elongated handle section may be configured in a manner similar to surgical retractors, and may be comprised of a plastic material if the entire surgical finger assembly is to be disposable.

Figure 2:
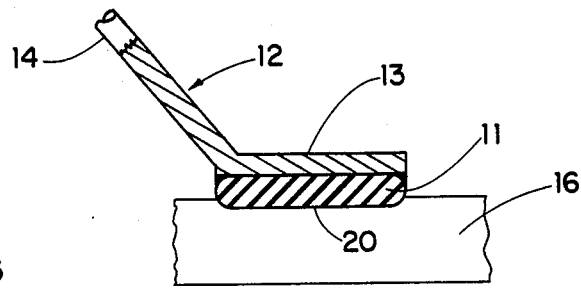
FIG. 2 is a partial, sectional view of the surgical finger assembly of FIG. 1, in contact with a blood vessel.
Figure 3:
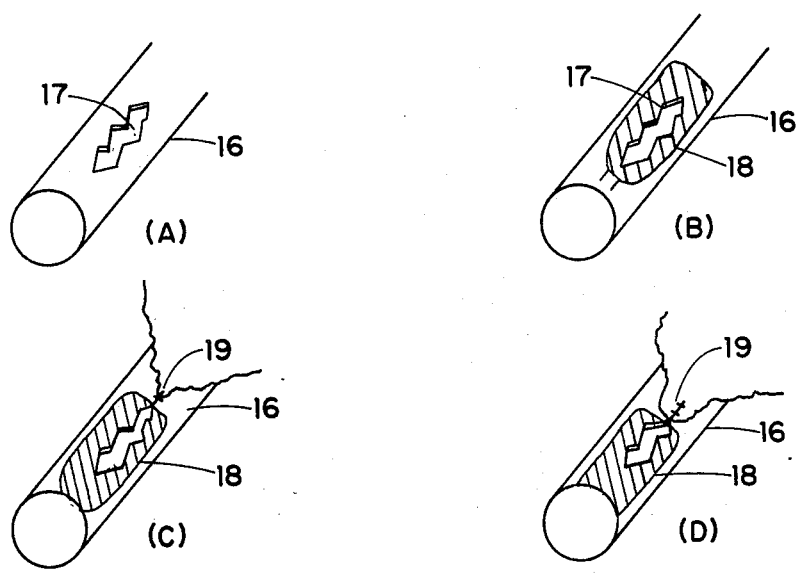
FIG. 3 illustrates four perspective views of a lacerated area of a blood vessel that include finger print configurations associated with the compressive contact between the surgical finger assembly of FIG. 1 and the blood vessel, during the surgical procedure of first controlling the bleeding therefrom, and the subsequent hemostatic suturing of the laceration.

The utility of the surgical finger assembly 10 is apparent from the following description in association with FIGS. 2 and 3. A surgeon confronted with bleeding from a blood vessel in the depths of a surgical or trauma induced wound, may introduce the support section 13 of the elongated handle 12 of the surgical finger assembly into the wound until the pliant finger tip member 11 engages a lacerated area of a blood vessel. The pliant character of the finger tip member 11 enables a pliant contact surface 20 thereof to conform with the surface of the blood vessel 16, and with the application of appropriate pressure, occludes the laceration 17 (See FIG. 2). As depicted in FIG. 3, the view designated (A) illustrates a blood vessel 16 having a laceration 17 through which blood is flowing. The view designated (B) illustrates the same blood vessel 16 and the laceration 17 of view (A), but includes a finger print 18, or area of continuous contact between the contact surface 20 of the plaint finger tip member 11 of the surgical finger assembly 10 and the blood vessel 16. This condition prevails when the pliant finger tip member 11 is first pressed against the complete laceration 17 to achieve occlusion. As illustrated in view (B) of FIG. 3, the finger print 18 completely encompasses the laceration 17. Upon occluding the laceration 17, the surgeon may gradually move the pliant finger tip member 11 in a direction longitudinal to the laceration 17 to progressively expose one end of the laceration 17 for the application of surgical sutures 19 thereto. Views (C) and (D) of FIG. 3 indicate, indirectly, the progressive movement of the pliant finger tip member 11 in a direction longitudinal to the laceration 17, by means of the relative positions between the laceration 17 and the finger print 18.

Figure 4:
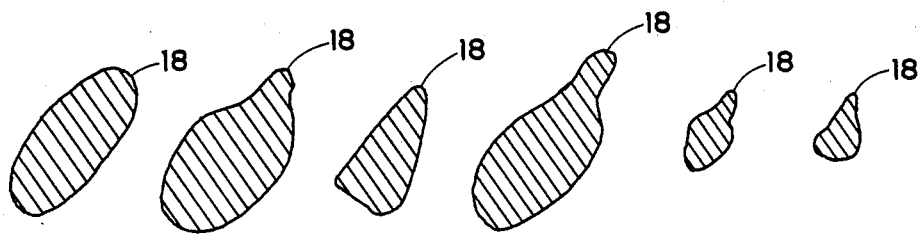
FIG. 4 illustrates alternate finger print configurations associated with alternate pliant finger tip members of the surgical finger assembly of FIG. 1.

As illustrated in FIG. 4, the finger print 18 may by the surgeon's selection from a plurality of differently configured finger tip members 11 (not shown), have one of a plurality of shapes and sizes to most efficaciously attend to the occlusion of a particular type of laceration.

While the invention has been described in connection with an exemplary embodiment thereof, it will be understood that many modifications will be apparent to those of ordinary skill in the art and that this application is intended to cover any adaptations or variations thereof. Therefore, it is manifestly intended that this invention be only limited to the claims and the equivalents thereof.

What is claimed:

1. A surgical finger assembly for direct application to an individual lacerated blood vessel in the depths of a surgical or trauma wound to control the immediate blood loss from the laceration, comprising:

a finger tip member prepared from pliant material, said finger tip member having a first pliant major surface dimensioned to be inserted unobstrusively into said wound, and to make direct contact with said blood vessel, and with a width dimension ranging up to general correspondence to the width of said blood vessel, said finger tip member capable of occluding substantially all of a lacerated area of the blood vessel in a continuous compressive manner; and an elongated handle having a support section at one end thereof and an elongated handle section extending to the other end thereof, said support section being attached to a second major surface of said finger tip member and corresponding in size thereto, said second major surface opposite to said first pliant major surface; for applying compressive forces directly against said blood vessel therethrough.

2. A surgical finger assembly in accordance with claim 1 wherein said elongated handle is of limited thickness and of extended length to permit the introduction of said pliant finger tip member into the depths of the surgical wound while taking up very limited space.

3. A surgical finger assembly in accordance with claim 1 wherein said support section is removably attached to said elongated handle section for rendering replaceable and disposable said support section and said finger tip member attached thereto.

4. A surgical finger assembly in accordance with claim 1 wherein said support section is removably attached to said second major surface of said finger tip member for rendering replaceable and disposable said pliant finger tip member.

5. A surgical finger assembly in accordance with claim 1 wherein said finger tip member is comprised of a fluid or gel-filled nonporous container formed of a silicone membrane.

* * * * *